United States Patent [19]

Fite et al.

[11] Patent Number: 5,142,143
[45] Date of Patent: Aug. 25, 1992

[54] METHOD AND APPARATUS FOR PRECONCENTRATION FOR ANALYSIS PURPOSES OF TRACE CONSTITUTES IN GASES

[75] Inventors: Wade L. Fite, Pittsburgh; Stephen M. Penn, Murrysville, both of Pa.

[73] Assignee: Extrel Corporation, Pittsburgh, Pa.

[21] Appl. No.: 784,068

[22] Filed: Oct. 30, 1991

Related U.S. Application Data

[63] Continuation of Ser. No. 606,935, Oct. 31, 1990, abandoned.

[51] Int. Cl.⁵ .............................................. G01N 35/06
[52] U.S. Cl. .................... 250/288; 250/281; 73/863.12; 73/864.81; 436/173; 436/178
[58] Field of Search .................. 250/288, 288 A, 281, 250/282; 73/863.12, 864.81, 31.01, 31.02, 31.03; 436/161, 173, 178; 422/83, 89

[56] References Cited

U.S. PATENT DOCUMENTS

| | | | |
|---|---|---|---|
| 3,318,149 | 5/1967 | Varadi | 250/288 A |
| 3,589,171 | 6/1971 | Haley | 250/288 A |
| 4,517,461 | 5/1985 | Grandall | 250/288 A |
| 4,732,046 | 3/1988 | Lawrence et al. | 250/282 |

*Primary Examiner*—Jack I. Berman
*Assistant Examiner*—Kiet T. Nguyen
*Attorney, Agent, or Firm*—Penrose Lucas Albright

[57] ABSTRACT

A preconcentrator for analyzing trace constituents in gases wherein a sample gas is introduced to a confined sorbent which thereafter is evacuated by a vacuum pump and a low-pressure carrier gas passes through the sorbent while it is desorbing, wherein the desorbed trace constituents are carried by the carrier gas to a detector that operates at low pressure such as a mass spectrometer. Because the mass of the carrier gas which carries the desorbed trace consituents to the detector is at a lower pressure and therefore has less density than the sample gas, the relative mass of trace constituents in the carrier gas is much greater than in the sample gas. The sample gas can be hot to assist desorption or a gas which reacts with trace constituents of interest to improve their detection. Valves located in the system between the sample gas intake, the carrier gas supply, the vacuum pump for the system and the detector operate to admit the sample gas, isolate the system, create a vacuum in the system, establish the sample gas flow, and to carry the trace consituents to the detector. Preconcentrators can be placed in parallel, whereby when one is desorbing and analyzing trace elements, the other is receiving the sample gas.

25 Claims, 5 Drawing Sheets

METHOD AND APPARATUS FOR PRECONCENTRATION FOR ANALYSIS PURPOSES OF TRACE CONSTITUTES IN GASES

This invention was made with Government support under Grant No. 2R44ES0515102, awarded by the National Institutes of Health. The Government has certain rights in the invention.

This is a continuation of application Ser. No. 07/606,935, filed Oct. 31, 1990, now abandoned.

FIELD OF THE INVENTION

This invention relates to the detection of trace constituents in air or other gases and, more particularly, to an improved method and apparatus for preconcentrating these constituents to provide a more sensitive detection and measurement. Although the invention may be used for any detector which fundamentally measures relative concentrations of gases wherein the pressure of the gas is reduced to below atmospheric pressure for analysis, its principal application is for use in mass spectrometry.

BACKGROUND OF THE INVENTION

Preconcentration is a well known technique in analytical chemistry and is used in the detection of trace contaminants in both gases and liquids. In the analysis of a gas, the gas, commonly at or near atmospheric pressure, is drawn through or past a sorbent which selectively adsorbs or traps the trace constituents. The adsorption usually takes place on the surface of a solid sorbent which in most cases is a powder, "wool" or sheet. Sorbents are selected on the basis of their ability to adsorb compounds of interest and their adsorbing capacity. The amount of trace constituent that is adsorbed is proportional to the time that the gas is drawn through or otherwise contacts the sorbent ("sampling time"), before the sorbent is saturated. Following the time period wherein the sampling takes place, the sorbent is induced to release the trace constituents, usually accomplished by rapidly heating the sorbent. The temperature of the sorbent may be raised sufficiently in one step so that all of the analytes are desorbed simultaneously ("flash desorption"), or it may be increased more slowly so that different chemical species, which desorb at different temperatures, are released at different times ("temperature programmed desorption"). In either case, the trace constituent is re-introduced into a carrier gas flow in a desorption interval of time that is much shorter than the period of time wherein the sampling was accomplished and, as a result, the concentration of the plug of analyte in the carrier gas is higher than was its concentration in the original sample gas. An example of a device that so operates is the Universal Automated Concentrator manufactured by Envirochem, Kemblesville, Pa.

It is common for the sorbent to be in the form of a powder confined within a thin-walled tube which is sufficiently granular for the gas to flow through it, and to provide that the flow of carrier gas through the sorbent during the desorption period is in an opposite direction to the flow through it during the sampling period. An example of a preconcentrator which employs this method is the Automatic Chemical Agent Monitor System (ACAMS), which was developed by Southern Research Institute for the U.S. Army and which is manufactured by ABB Process Analytics (formerly Combustion Engineering, Inc.), of Lewisburg, W. Va., and CMS Research Corporation of Birmingham, Ala.

Preconcentrators also are used in the analysis of volatile compounds in liquids, typically water, by using "purge and trap" techniques. For this, an inert gas is bubbled through the liquid to entrain the volatile contaminants and carry them to a sorbent similar to the ones described above for gas samples. After the sampling (purging and trapping) is complete, the analytes are desorbed from the sorbent, as described above. The Tekmar LSC 2000, manufactured by Tekmar Company of Cincinnati, Ohio, is an example of a commercially available "purge and trap" instrument.

Preconcentrators are commonly used in conjunction with gas chromatographs (GC) to separate and identify the analytes. The flow rate of the carrier gas through the preconcentrator (or the final trap) during the desorption phase, in general, is determined by the characteristics of the GC column. Capillary columns, for example, use lower mass flow rates than traditional packed columns. In addition, to increase the resolution and sensitivity of the GC, the desorbed analytes are often retrapped, usually by cryogenic means, at or near the entrance of the CG column, from which they are desorbed rapidly to ensure that the sample is injected into the column in a short period of time. The Tekmar LSC 2000 "purge and trap" device is used with commercially available gas chromatographs using packed and megabore columns, and the Tekmar Model 1000 capillary interface, which employs cryogenic refocusing, allows the Tekmar LSC 2 "purge and trap" device to operate with capillary column gas chromatographs.

The following Publications are cited for more comprehensive explanations of prior art apparatus and techniques mentioned above, and are incorporated herein by reference:

1. SW-846, "Test Methods for Evaluation of Solid Waste," Third Edition, EPA Publication OSW 0000846; Methods 0030 and 5040.
2. D. L. Fox, Anal. Chem. 61. IR (1989), and references within.
3. D. L. Fox, Anal. Chem. 59, 280R (1987), and references within.
4. R. A. Kagel and S. O. Farwell, Anal. Chem. 58. 1197 (1986).
5. P. A. Steudler and W. Kijowski, Anal. Chem. 56, 1432 (1984).
6. R. Otson, J. M. Leach, and L. T. K. Chung, Anal. Chem. 59. 58 (1987).
7. T. Bellar and J. Lichtenberg, J. Am. Water Works Assoc. 66, 739 (1974). 8. United States Environmental Protection Agency, "Method 524.2. Volatile Organic Compounds in Water by Purge and Trap Capillary Column Gas Chromatography/Mass Spectrometry," August, 1986.
9. N. Kirshen, Am. Lab. 16 (12), 60 (1984).
10. L. D. Landau and E. M. Lifshitz, "Fluid Mechanics," Translated by J. B. Sykes and W. H. Reid, Pergamon Press, London, 1959, p. 59.

SUMMARY OF THE INVENTION

In existing apparatus, the carrier gas into which the analytes are ultimately desorbed is generally, if not always, at, near or above atmospheric pressure on the higher pressure side of the final trap. An important aspect of the instant invention is the use of substantially reduced pressures on both sides of the trap, as well as low volume flows and short times, during the desorption period to increase the concentration of the analyte in the carrier gas.

In considering the theory of preconcentrators, the total number (N) of trace constituent molecules taken from a sample of gas and adsorbed on an ideal preconcentrator is represented by:

$$N = f_s n_s W_s t_s. \tag{1}$$

where $f_s$ is the fractional molecular concentration of trace constituent in the gas, $n_s$ is the number density of air molecules (cc$^{-1}$), which is proportional to the pressure of the gas entering the preconcentrator, $W_s$ is the volume flow rate entering the preconcentrator (cc/sec) and $t_s$ is the sampling time (sec). The same total number (N) of molecules are released from the preconcentrator during the desorption phase, i.e.:

$$N = f_d n_d W_d t_d \tag{2}$$

where the parameters have the same meanings as in equation (1) except for being appropriate to the desorption phase and with $n_d$ and $W_d$ being the number density and volume flow rate of gas, respectively leaving the preconcentrator. The subscripts "s" and "d" as used herein, identify "sample" and "desorption" symbols respectively in the equations. The combination of equations (1) and (2) defines a preconcentration factor, or "gain," (G) as the ratio of the molecular concentrations of the trace constituent during the desorption and sampling phases:

$$G = \frac{f_d}{f_s} = \frac{n_s}{n_d} \times \frac{W_s}{W_d} \times \frac{t_s}{t_d} \tag{3a}$$

In an ideal gas, the following equation is applicable:

$$p = nkT = \rho \frac{kT}{m} \tag{4}$$

where P is the pressure, k is Boltzmann's constant, T is the temperature in °K. P is the mass density (gm/cc) n is the number density and m is the molecular mass. Therefore equation (3) may be alternatively expressed as:

$$G = \frac{f_d}{f_s} = \frac{P_s}{P_d} \times \frac{W_s}{W_d} \times \frac{t_s}{t_d} \tag{3b}$$

$$= \frac{\rho_s}{\rho_d} \times \frac{W_s}{W_d} \times \frac{t_s}{t_d} \tag{3c}$$

The mass flow of gas (Q) is the product of the mass density and the volume flow rate of Q=ρW. G can therefore also be defined:

$$G = \frac{Q_s}{Q_d} \times \frac{t_s}{t_d} \tag{5}$$

where the subscripts "s" and "d" again refer to the sampling and desorption periods, respectively.

In viscous flow, the mass flow of a compressible gas through a restriction such as a tube or channel is, to good approximation under isothermal conditions, proportional to the difference of the squares of the pressures at the high- and low-pressure ($P_o$ and $P_f$, respectively) ends of the restriction and therefore:

$$Q = \frac{K}{2}(P_o^2 - P_f^2) \tag{6}$$

$$= K \frac{(P_o - P_f)}{2}(P_o - P_f) \tag{7}$$

$$= K <P> \Delta P. \tag{8}$$

In equations (6) and (7), $P_o - P_f$ is the pressure difference between the ends of the tube which difference is expressed as "$\Delta P$" in equation (8). Also in equation (8), $<P>$ is the algebraic average pressure in the tube $(P_o + P_f)/2$ in equation (7). K, in equations (6), (7l) and (8l), is a factor that is dependent on the geometry of the tube and the coefficient of viscosity of the gas. Because the coefficient of viscosity of a gas is independent of its pressure, factor K is a constant.

The combination of equations (5) and (8l) yields an expression for the gain (G) in terms of the average pressure in the tube and the pressure drop across it during the sampling and desorption phases:

$$G = \frac{Q_s}{Q_d} \times \frac{t_s}{t_d} = \frac{<P>_s \Delta P_s}{<P>_d \Delta P_d} \times \frac{t_s}{t_d} \tag{9}$$

To maximize the gas flow during the sampling phase, the gas can be pumped at a sufficient velocity so that the pressure at the preconcentrator exit end is effectively zero. In such case, $<P>_s P_s/2$ and $\Delta P_s = P_s$, where $P_s$ where $P_s$ again is the pressure at the entrance of the sorbent during the sampling. By substituting these into equation (8), the following formula results:

$$Q_s = \frac{K}{2} P_s^2 \tag{10}$$

Accordingly, equations (5) and (10) combine to provide a relatively simplified expression for the gain:

$$G = \frac{Q_s}{Q_d} \times \frac{t_s}{t_d} = \frac{1}{2} \times \frac{P_s^2}{<P>_d \Delta P_d} \times \frac{t_s}{t_d} \tag{11}$$

As an example, if the sampling is at atmospheric pressure ($P_x$ = 760 l Torr) and the pressure difference across the preconcentrator during the desorption phase is say, 100 torr, with the pressure at the low-pressure end being 40 torr, then the preconcentration factor, G, would be 32, even if the sampling and desorption times are equal.

If, during the desorption phase, the pressure drop across the tube is such that $\Delta P_d$, is much greater than the pressure at the low-pressure end of the sorbent, $<P>_d$, then $<P>d = \Delta P_d/2$; and the expression for the gain is further simplified to:

$$G = \frac{Q_s}{Q_d} \times \frac{t_s}{t_d} = \left(\frac{P_s}{\Delta P_d}\right)^2 \times \frac{t_s}{t_d} \tag{12}$$

From the foregoing equations, it should be appreciated that by providing different pressure and gas flow rates wherein the higher pressure and higher volume flow rate takes place in the sampling phase of the gas and a much lower pressure and lower volume flow rate are used during the desorption phase, substantially greater gaseous and vapor preconcentrations can be achieved which are adaptable for analysis by mass spectrometers.

The invention utilizes this concept by exposing an activated sorbent to the sample of gas or vapor to be analyzed at or near atmospheric pressure, the sorbent being in a confined space which is then sealed off and the pressure therein is reduced. Next, the sorbent is heated to desorb its previously adsorbed constituents into a low pressure gas flowing within the sealed space to carry those constituents to the ionizing chamber of a mass spectrometer or other low pressure detector which then analyzes them. If the desorption time is less than that required for adsorption, a further concentration of the gases and vapors of interest occurs.

Adaptabilities and capabilities of the invention will be more fully appreciated by those skilled in the art as the description progresses, reference being had to the accompanying drawings, in which:

DESCRIPTION OF THE PREFERRED EMBODIMENTS

Figure 1:
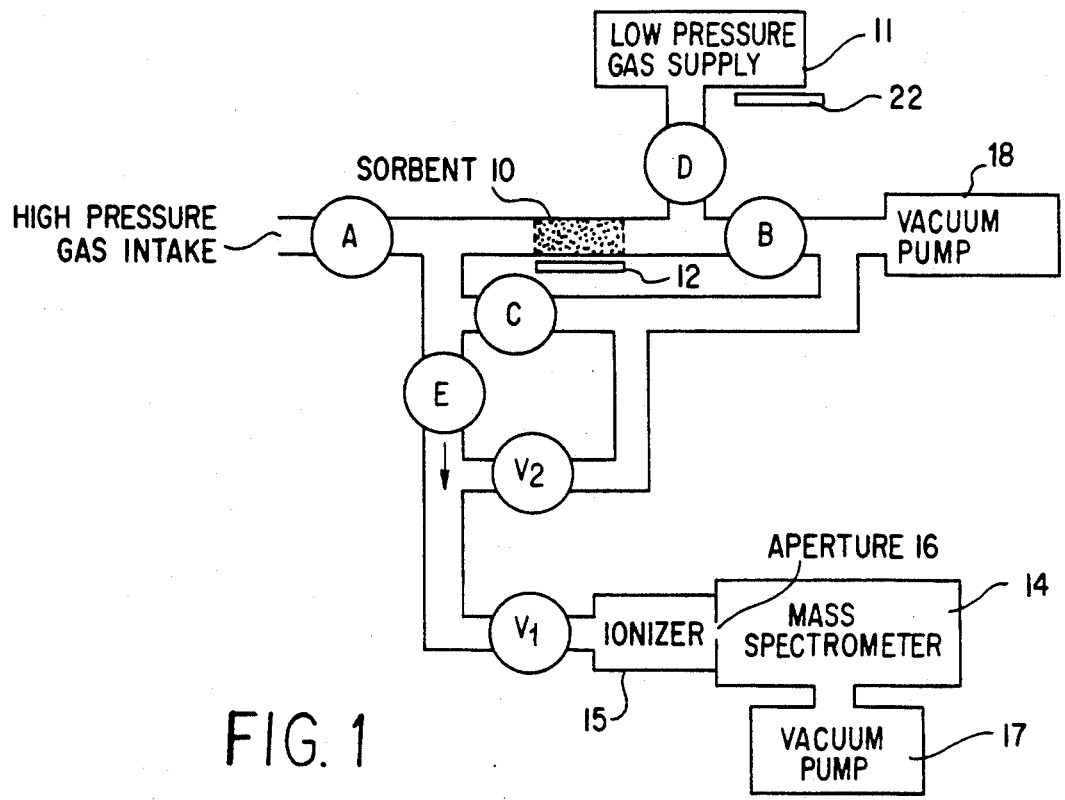
FIG. 1 illustrates in diagrammetric form a preferred embodiment of the invention, where the preconcentrator comprises a tube that contains the sorbent material, which when cool adsorbs the trace constituents and when heated releases them back into the vapor phase, the low-pressure detector being shown as a mass spectrometer.

Referring to FIG. 1, valves $V_1$ and $V_2$ are variable leak valves. Valve $V_2$ is used to adjust the gas mass flow rate through the sorbent 10 during the desorption phase and, in conjunction with the pressure in the low-pressure gas supply, the desorption period pressure $P_d$. Valve $V_1$ is a variable leak valve leading to the mass spectrometer 14 or other low-pressure detector and is adjusted to transmit a sufficiently small sample of the desorption gas flow from valve E to valve $V_1$ that can be handled by the vacuum system provided by a vacuum pump 17 of the mass spectrometer 14 or other low-pressure detector. Valves A, B, C, D and E are high conductance valves that are either opened or closed as described hereinafter.

During the sampling phase valves A and B are opened and C, D and E are closed. Gas usually at atmospheric pressure, is drawn through the sorbent 10, which here is shown as a granular powder inside a tube, toward vacuum pump 18. After a given sampling time, $t_s$, valve A is closed and valve C is opened with valve B remaining open, and vacuum pump 18 lowers the pressure in the sorbent tube section 10. The purpose of the bypass containing valve C is to allow rapid pumpdown of the volume to the left (as seen in FIG. 1) of the sorbent tube section 10. This bypass is not essential, in that sorbent tube section 10 would eventually be pumped down, but all the gas to the left of sorbent tube section 10 would have to be pumped through the sorbent which is an obstruction to the gas flow. Without the bypass the period of time to complete the preconcentration sequence is slightly longer.

When sufficient vacuum exists in sorbent tube section 10, valves B and C are closed, valve D is opened and gas from a low-pressure gas supply 11 enters sorbent tube section 10. Valve E is opened, either simultaneously with valve D or shortly thereafter, and low-pressure gas flows through sorbent 10. After the flow is established, the sorbent tube is rapidly heated by a heating device 12 and trace constituents adsorbed by sorbent 10 are released and enter the low-pressure gas flow. A portion of this flow is split off and enters the mass spectrometer 14 or other low-pressure detector via variable leak valve $V_1$ and ionizer 15. Valves A and B are opened and C, D and E are closed. Heating device 12 may comprise an electrically energized heater ribbon wrapped around sorbent tube section 10, but other heating means will be apparent to those skilled in the art. Mass spectrometer 14 is evacuated by vacuum pump 17. Ionizer 15 may be located within a chamber which is evacuated by another vacuum pump (not shown) in a differential pumping arrangement.

The desorption time, $t_d$, is that period of time required to desorb all trace constituent that were adsorbed during the sampling time. This period of time can be controlled within limits by varying the rate of heat flow to the sorbent tube 10. More rapid heating produces a smaller $t_d$ and therefore, as set out in equation (5), a higher gain factor, G.

The period of time during which trace constituents enter ionizer 15 is independent of the desorption gas flow rate. For example, using a slower desorption gas volume flow rate at a given pressure will produce a higher number density (or partial pressure or fractional concentration) of trace constituents in the desorption gas flow because they are distributed over a shorter distance along the flow and a larger signal will result. But, this shorter length of trace constituents in the gas flow is received through valve $V_1$ in the same length of time $t_d$ because of the slower linear flow speed.

Nevertheless, the volume flow rate does determine the period of time required to transport the desorbed analyte from the sorbent 10 to the entrance of the mass spectrometer 14 at valve $V_1$. The linear velocity of the carrier gas, which determines the transit time, is proportional to the volume flow rate. High linear velocities and low mass flow rates occur simultaneously under the low-pressure desorption conditions.

The response of the mass spectrometer 14 shown in FIG. 1 to the desorbed analytes is also affected by the volume of ionizer 15 and the pumping speed of the aperture 16 that separates ionizer 15 and mass spectrometer 14. For example, consider the case in which desorbed analyte entering the ionizer 15 immediately diffuses throughout ionizer 15. The analyte concentration in ionizer 15, $f_i(t)$, increases exponentially during the time period that the analyte enters the ionizer ($0 \leq t \leq t_d$):

$$f_i(t) = f_d(1 - e^{-t/\tau}) \tag{13}$$

where $f_d$ is the analyte concentration in the desorption gas flow and $\tau$ is a time constant characteristic of the ionizer. Once the slug of gas containing the analyte has passed the entrance to valve $V_1$ ($t \geq t_d$), the concentration in the ionizer falls exponentially from its peak value, $f_i(t_d)$, with the same time constant $\tau$:

$$f_i(t) = f_i(t_d) e^{-(t - t_d)/\tau} \tag{14}$$

Time constant $\tau$ in equations (13) and (14) is the ratio of the ionizer volume, $V_i$, to the pumping speed, $S_i$, (in units of volume per unit time) out of ionizer 15, thus:

$$\tau = V_i / S_i \tag{15}$$

In FIG. 1, ionizer 15 is pumped only through aperture 16 that separates ionizer 15 from mass spectrometer 14.

If the ionizer's time constant $\tau$ is small compared to the desorption time $t_d$, then the analyte concentration in ionizer 15 rapidly approaches and follows the analyte concentration $f_d$ in the carrier gas. Conversely, if the time constant $\tau$ is much larger than the desorption time $t_d$, then the concentration in ionizer 15 rises during the period of time analyte enters ionizer 15 to only a fraction of the concentration in the carrier gas:

$$f_i(t_d) = f_d(1 - e^{-t_d/\tau}) \simeq f_d t_d / \tau \tag{16}$$

The concentration then falls with the characteristic time constant $\tau$ according to equation (14).

Figure 2:
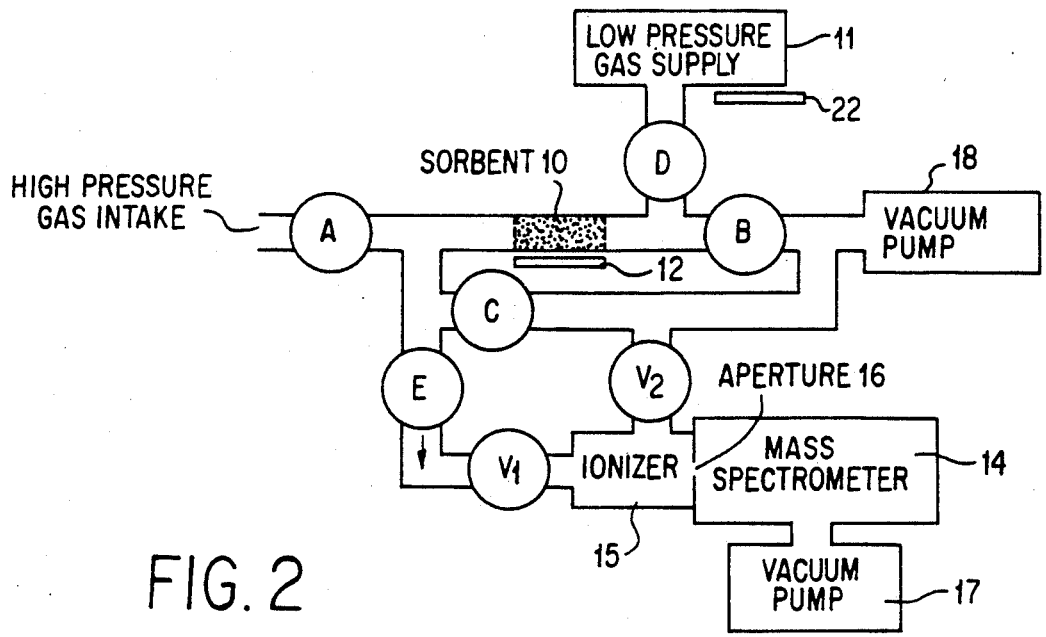
FIG. 2 represents an alternative arrangement of a preconcentrator in combination with a mass spectrometer in accordance with the invention.

Ionizers used for electron-impact (EI) and chemical ionization (CI) typically have small volumes and sufficiently large apertures whereby their time constants $\tau$ are less than the typical desorption times (a few seconds) and the arrangement shown in FIG. 1 is satisfactory. Some discharge ionization sources, however, require large volumes and moderately high pressures to allow their plasmas to be recombination limited. In such event, the arrangement illustrated in FIG. 2 is preferred wherein all of the desorption gas is directed to flow through the ionizer and the gas flow rate through such ionizer 15 is increased.

For FIG. 1, a suitable valving sequence for sampling air or other gas, and concentrating the trace elements for subsequent analysis by a mass spectrometer, is set forth in Table I.

TABLE I

Valves A, B, C, D and E are on/off valves. Using "1" to designate a valve that is open and "0" to designate that a valve is closed, the valving sequence is as follows:

| Phase | Valves | | | | | Sorbent Heat 12 | Process |
|---|---|---|---|---|---|---|---|
| | A | B | C | D | E | | |
| 1. | 0 | 1 | 0 | 0 | 0 | Off | Initial pumpdown. |
| 2. | 1 | 1 | 0 | 0 | 0 | Off | Sampling of air. |
| 3. | 0 | 1 | 1 | 0 | 0 | Off | Reduce pressure. |
| 4. | 0 | 0 | 0 | 1 | 1 | Off | Establish desorption gas flow. |

TABLE I-continued

Valves A, B, C, D and E are on/off valves. Using "1" to designate a valve that is open and "0" to designate that a valve is closed, the valving sequence is as follows:

| Phase | Valves | | | | | Sorbent Heat 12 | Process |
|---|---|---|---|---|---|---|---|
| | A | B | C | D | E | | |
| 5. | 0 | 0 | 0 | 1 | 1 | On | Desorption of Analytes. |

In the arrangement of FIG. 2, valves A, B, C, D and E operate as in FIG. 1 and valves $V_1$ and $V_2$ are adjusted to produce the desired desorption mass flow as well as the appropriate pressure in the ionizer.

In either arrangement (FIGS. 1 and 2), the low-pressure desorption gas need not be the same gas as the original gas that entered the preconcentrator. Indeed it is often desirable to use a low-pressure desorption gas that is chemically different from the gas being sampled. For example, trace constituents in some air samples may react with oxygen at elevated temperatures. If air is also used as the desorption gas, the desorbed analytes may react with oxygen in air heated in the desorption process, and produce different species. The use of an inert gas such as argon or a fully oxided gas such as carbon dioxide may be desirable in these cases. Conversely, a reactive carrier gas can be advantageously used to detect a derivative of the original analyte or to distinguish compounds that have similar mass spectra based on their reactivity or reactive pathway with the desorption gas, or to produce a species that is more easily ionized. In addition, when using chemical ionization (CI) as the ionization method, the chemical ionization reagent gas may also be the desorption gas.

The use of preheated low-pressure desorption gas that is preheated by preheater 22 contributes thermal energy to raise the temperature of the adsorbent in sorbent tube section 10, thus either reducing the period of time to effect desorption therefrom, or reducing the heating load of heating device 12. The heat capacity of the low-pressure desorption gas is usually considerably less than that of the sorbent material in tube section 10. Nevertheless, because the low thermal conductivity of many sorbent materials results in the thermal activity caused by hot desorption gas being concentrated at their surfaces from whence the molecules desorb, the pre-heated desorption gas may provide a more effective contribution to the desorption process than otherwise might be expected.

The arrangements of FIGS. 1 and 2 assume the desorption mass flow is sufficiently large and that the capacity of the mass spectrometer 14 or other low-pressure detector is such that only a small portion of the desorbed gas can be received through aperture 16 for analysis, the gas handling capacity of the mass spectrometer or other detector being the limiting feature. If the desorption gas mass flow is sufficiently low, and the pumping capacity of the mass spectrometer's vacuum pumps is high, then all the desorption gas flow can be taken via aperture 16 and ionizer 15 into mass spectrometer 14. In such case, the valve $V_2$ can be closed or an alternative arrangement as shown in FIG. 3 may be substituted.

Figure 3:
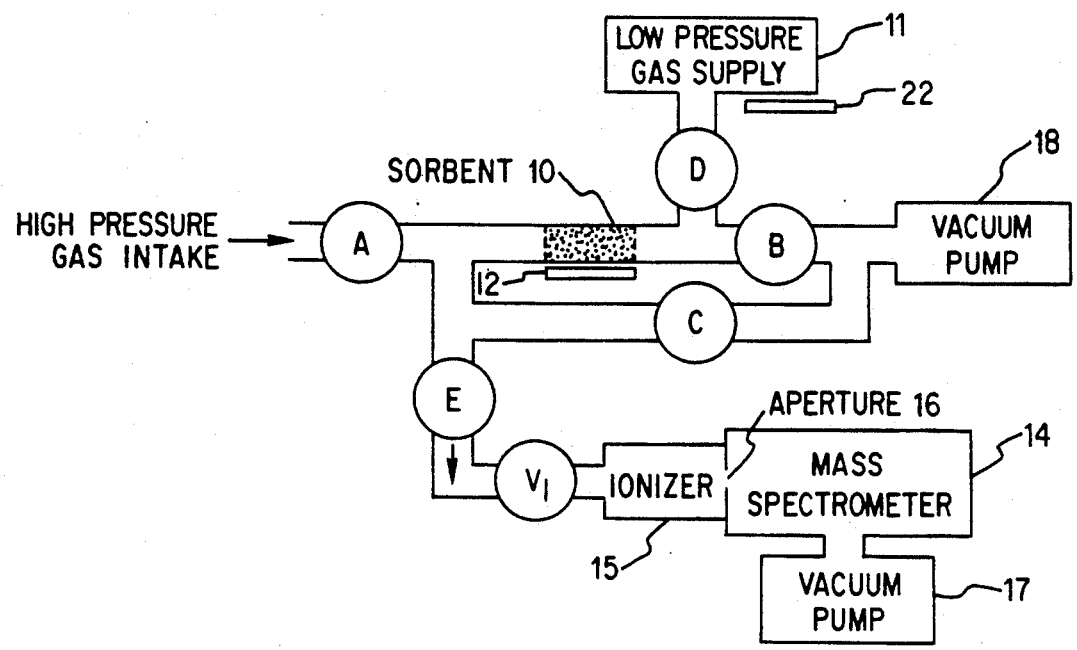
FIG. 3 is a further diagrammatic arrangement of a preconcentrator combined with a mass spectrometer wherein all of the desorbed concentrated constituents are received by the mass spectrometer.

In the arrangement illustrated in FIG. 3 the sequence of opening and closing valves A, B, C, D and E is the same as for FIGS. 1 and 2. Vacuum pump 17 is a high-speed pump (several hundred liters/sec, typically) that normally maintains the pressure in the mass spectrometer in the range of $10^{-5}$ torr. The difference here is that now all the desorption gas and therefore all the trace constituents adsorbed by the sorbent enter ionizer 15 of mass spectrometer 14 and then are received in mass spectrometer 14 itself through its aperture 16. The actual mass flow rate into a typical mass spectrometer is of the order of $10^{-3}$ torr-liters/sec or about 0.1 atm-cc/min, and the same mass flow rate of desorption gas is thus the maximum amount that should be permitted to flow through the sorbent 10. In this case, the adjustable valve $V_1$ and the pressure provided by the low-pressure desorption gas supply govern the desorption pressure and the actual mass flow.

Figure 4:
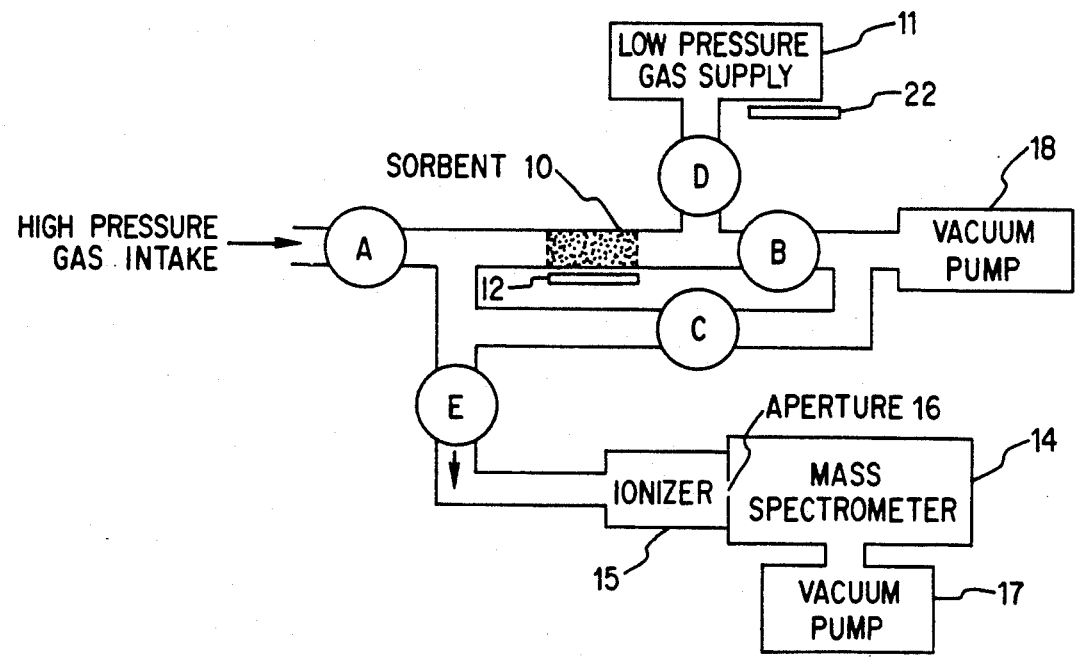
FIG. 4 is a still further diagrammatic representation of the invention wherein electron impact or chemical ionization occurs in the ionizer, and the desorption pressure is matched to the ionizer pressure.

For a very low desorption pressure as well as very low desorption gas mass flow, either valve $V_1$ should be wide opened or eliminated as shown in FIG. 4.

If one uses an electron-impact (EI) or chemical ionization (CI) ionizer 15, both of which usually operate at pressures less than one torr, then the configuration of FIG. 4 is acceptable if the trace constituents do not tend to be adsorbed on the interior walls of the conduits between sorbent 10 and ionizer 15 or on surfaces inside the valve E. But, if the trace constituents do tend to stick to these surfaces, then the configuration of FIG. 3 is preferable because the low-pressure gas supply and valve $V_1$ can be set to maintain a higher pressure between the sorbent and valve $V_1$, which inhibits diffusion of the trace constituents to the conduit walls.

According to equation (5), the relative gain in concentration depends on the ratio of the mass flow during the sampling phase to that in the desorption phase. Diffusion losses and the flow requirements of the detection method ultimately determine the minimum acceptable desorption mass flow. Therefore the mass flow during the sampling period, $Q_s$, should be as large as possible to maximize the gain. The absolute mass flow during the sampling period is determined by the factor K in equation (6), which relates the mass flow, Q, of a preconcentrator to the difference of squares of the pressures at the two ends of the preconcentrator. This factor clearly depends on geometry the length and inside diameter in the case of a tube. To obtain a high mass flow rate during sampling, a preconcentrator tube should be short.

Use of a short tube, however, leads to the possibility that during the sampling phase the adsorption sites on the sorbent will become completely filled and the sorbent will not adsorb all the trace constituents during the sampling phase. In such event, the sorbent is saturated and trace constituents in the sample gas thereafter flowing through the sorbent are not reflected in the analyte concentration during the desorption phase, even if they were within the sampling mass flow or the sampling time $t_s$. A solution is to decrease the sampling time until G becomes proportional to $t_s$. Alternatively, if one seeks to keep G high, the preconcentrator can be replaced with one of a larger geometry (length and diameter in the case of a tubular preconcentrator) at the possible cost of increasing the desorption time, $t_d$, because the conduction of thermal energy from preheater 12 or 22 to the center of the tube will be affected by the geometry change.

A major problem with commonly used preconcentration techniques is that they rely primarily, and often only, on the ratio of sampling to desorption times. Because a certain period of time is required for measurements on the preconcentrated sample which determines the minimum desorption time, it follows that the length of time needed to achieve a specified preconcentration factor must be relatively large. Mathematically this can be expressed as $t_s = G t_d$.

Consider for example, a mass spectrometer wherein about 0.1 sec is required to make a mass scan over the range of a few hundred daltons. Because it typically takes about two seconds to drive off the adsorbed gas from a small sorbent tube, the mass spectrometer can make a number of scans over the time that the desorption gas is present. For a concentration gain factor of, say, 120, in a conventional preconcentrator the sampling time, $t_s$, must be around $120 \times 2$ sec = 240 sec = 4 minutes. In contrast, with the instant invention, using a desorption pressure of 40 torr and a desorption pressure drop of 100 torr (the case calculated above), and with a desorption time $t_d = 2$ sec, equation (11) indicates that a sampling time of only 7.5 seconds is required to achieve a desired gain factor of 120 and the total measurement time (sampling plus desorption times, plus another one or two seconds for switching the valves) is about ten to twelve seconds, neglecting pressure transient times after valves are opened and closed, rather than the four minutes total measurement time in the conventional preconcentrator case.

It is important in considering the total length of time required to analyze a given sample, that transients be considered when the gas flows required for the processes are modified by being commenced, stopped or reversed, or by having their pressures or velocities changed. In general, when a volume of gas is being evacuated through a tube and the pressure is such that viscous flow occurs, the pressure in the volume as a function of time, p(t), is given theoretically by:

$$P(t) = P_o \frac{1}{1 + \frac{\pi a^4 P_o t}{16 \eta V L}} \quad (17)$$

where $P_o$ is the initial pressure, a and L are the inner radius and length of the tube, V is the volume and $\eta$ is the viscosity of the gas. If one is pumping air ($\eta \approx 10^{-4}$ poise) from atmospheric pressure ($P_o = 760$ torr $\approx 1 \times 10^6$ dynes/cm$^2$) through a tube of $\frac{1}{8}$" diameter ($a \approx 0.15$ cm) that is 30 cm long, the time it takes to pump down a volume of 100 cm$^3$ to a pressure of 0.01 atmospheres is:

$$t_{.01} = 99 \times \frac{16 \eta V L}{\pi a^4 P_o} \approx 0.3 \text{ seconds.} \quad (18)$$

This calculation illustrates that, because pump-down and let-up times should be of the order of one second or less, it is necessary to use valves with small dead volumes and keep the lengths of lines short.

Figure 1A:
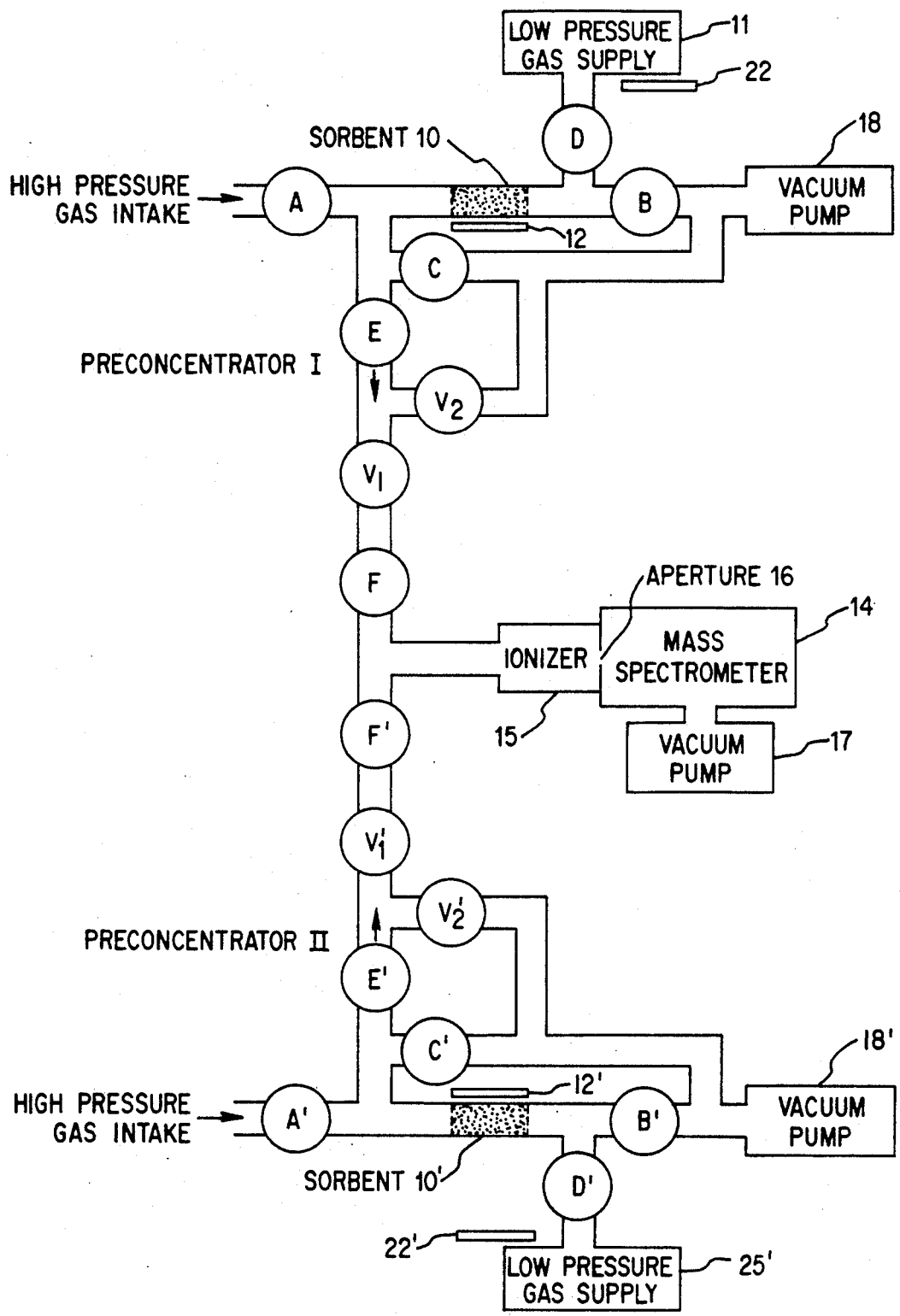
FIG. 1a is similar to FIG. 1 except that two preconcentrator arrangements are connected to the mass spectrometer.

One of the most time-consuming aspects of the measurement cycle is the cool-down time after the trace constituents have been thermally desorbed. Forced cooling can be accomplished by causing a cool gas to flow through the sorbent tube while blowing cool air along its exterior, or by circulating a liquid coolant around the tube. Other means such as Peltier Cooling may be employed, however, as are well known to those skilled in the art. But, whatever means are used, they consume time and complicate the construction of the device. An alternative approach is to provide two or more preconcentrators in parallel and to switch between them. One is in use while the other(s) are cooling. An apparatus for doing so is illustrated in FIG. 1a. Here valves F and F' provide that one preconcentrator may be operated while the other is being cooled and vice versa. Certain elements can be shared such as low pressure gas supply sources 11 and 11', vacuum pumps 18 and 18', and the high pressure intakes. By sharing splitter valves $V_1$ and $V_1'$, and $V_2$ and $V_2'$, valves F and F' may be eliminated and valves E and E' can be used to switch the flows alternatively from the preconcentrators I and II to the mass spectrometer 14 via aperture 16 and ionizer 15.

Figure 5:
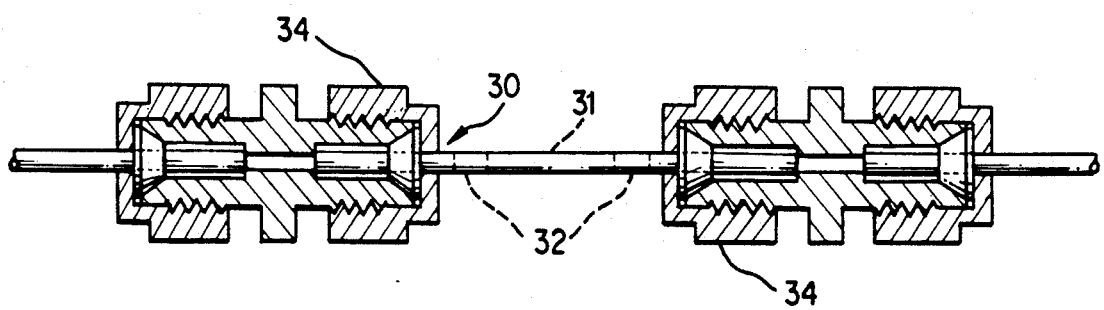
FIG. 5 is a detailed cross-sectional view of a sorbent tube as used in the invention.

A preconcentration concept in accordance with the invention was successfully implemented with mass spectrometry in April, 1990, at Extrel Corporation in Pittsburgh, Pa. The test apparatus was similar to the device shown in FIG. 1, in which the preconcentrator was of the sorbent tube configuration as shown in FIG. 5.

The sorbent tubes 30 used here were plain microhematocrit capillary tubes (Fischer Scientific Co., Pittsburgh, Pa.; cat. no. 02-668-68), which were thirty-seven millimeters in length having inside diameters of approximately of 1.5 mm and wall thicknesses of approximately 0.1 mm. The very thin wall of these tubes allows rapid heating and cooling of the sorbent 31. The capillary tube was packed with a one centimeter long section of mesh 60/80 Chromasorb 106 sorbent (TM Manville, purchased from Alltech Associates, Inc., Applied Science Labs, Deerfield, Ill.), which was held in place by pieces of silanized glass wool 32 tightly packed to a length of three millimeters on each end of the sorbent material. A nichrome ribbon (not shown) wrapped around the sorbent tube served as a resistive heater 12 for desorbing the adsorbed analyte. A type J thermocouple junction spot welded on the nichrome ribbon measured the temperature of the ribbon, and a temperature controller (Model 550, Fenwall) regulated its temperature during the desorption period. The sorbent tube was sealed to the rest of the apparatus by 1/16" Swagelok fittings 34 (TM Crawford Fitting Co.) and Teflon ferrules.

remaining plumbing, as shown in FIG. 1, comprised ⅛" tubing (stainless steel and Teflon), ⅛" Swagelok fittings 34, Teflon solenoid valves (Part 2-10-900, General Valve Corporation, Fairfield, N.J.; and Model 20-1-3, Valcor Engineering Corp., Springfield, N.J.), and stainless steel needle valves (Models SS22RS2, Whitey). A Hitachi 160VP CuteVac (174 L/min) served as the vacuum pump 18 shown in FIG. 1, and the pressures of the gases on each side of sorbent 10 in FIG. 1 were measured with a manometer (Baratron type 122AA-01000DB, MKS Instruments, Inc., Burlington, Mass.). This manometer was connected to the preconcentrator through stainless steel toggle valves (not shown in FIGS. 1-4), which generally remained closed during the entire preconcentration procedure to avoid excess volume in the preconcentrator. Pressure measurements generally were taken only while setting up a particular preconcentration sequence.

The low pressure gas supply for the desorption period was provided by two needle valves connected in series between ambient air and the vacuum pump 18. The region between the needle valves was connected to valve D, and the needle valves were adjusted to produce the desired pressure at the sorbent. Sufficient gas flow was maintained through the needle valves to ensure that gas flow through sorbent 10 did not affect the pressure applied to the sorbent. This arrangement is analogous to a stiff voltage divider in electronic circuitry. A vacuum regulator (Model 3491, Matheson, for example) constitutes another approach which may be employed.

The mass spectrometer 14 used in these experiments was a differentially pumped, single quadruple instrument (SpectrEL, Extrel Corporation, Pittsburgh, Pa.). The first vacuum chamber of the mass spectrometer, which houses the ion source, was pumped by a 450 L/S turbomolecular pump, the pumping speed of which was limited to about 150 L/S by its connection to the chamber. A 320 L/S diffusion pump pumped the rear vacuum chamber, which housed the quadruple mass filter. All of the experiments reported below were conducted using an electron-impact ion source operating with 70-eV electrons.

An external timer (ChronTrol, Lindburg Enterprises, Inc., San Diego, Calif.) controlled the operation of the solenoid valves in the preconcentrator. One timing sequence used to investigate the preconcentrator's behavior is set forth in Table II below, again using "1" to designate a valve that is open and "0" to designate that a valve is closed.

TABLE II

| Phase | Valves | | | | | Sorbent Heat | Process | Duration |
| --- | --- | --- | --- | --- | --- | --- | --- | --- |
| | A | B | C | D | E | | | |
| 1. | 0 | 1 | 0 | 0 | 0 | Off | Initial pumpdown. | 2 sec |
| 2. | 1 | 1 | 0 | 0 | 0 | Off | Sampling of air. | 3 sec |
| 3. | 0 | 1 | 1 | 0 | 0 | Off | Reduce pressure. | 2 sec |
| 4. | 0 | 0 | 0 | 1 | 1 | Off | Establish flow. | 3 sec |
| 5. | 0 | 0 | 0 | 1 | 1 | On | Desorb analytes. | 10 sec |
| | | | | | | | TOTAL | 20 sec |

The sampling time in this sequence was three seconds and the total cycle time (excluding the time required to cool the sorbent after desorption) was twenty seconds.

Figure 6:
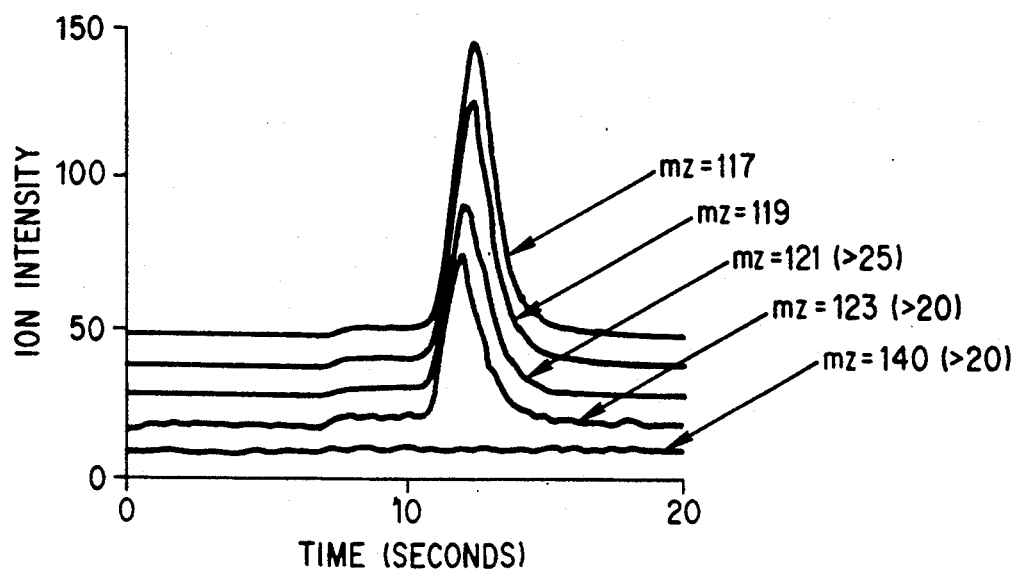
FIG. 6 is a graph of desorption profiles of the different isotropic fragmentations from a trace of carbon tetrachloride ($CCl_4$); in air

Experiments using this timing sequence were carried out with air doped with varying amounts of carbon tetrachloride ($CCl_4$). FIG. 6 shows the mass spectrometer signals recorded as a function of time during a preconcentration cycle in which air containing a total $CCl_4$ concentration of 3.4 parts per million (ppm) was sampled. Valve E to the mass spectrometer (FIG. 1) was opened about seven seconds into the scan, and a slight increase in the signals was seen at that time. About ten seconds into the scan, the sorbent 10 was heated causing the adsorbed analytes to desorb rapidly. The data recorded at masses 117, 119, 121, and 123 daltons, major peaks in the mass spectrum of $CCl_4$, show significant responses shortly thereafter, and the desorption profiles are approximately two seconds in duration (measured as the full width at half intensity). For comparison, the response at 140 daltons, a background mass not associated with $CCl_4$, shows little response.

The mass peaks at 119, 121 and 123 daltons correspond to fragment ions of $CCl_4$ molecules that contain one or more $^{37}Cl$ atoms. Based on the isotopic abundance of $^{37}Cl$, the signal at 123 daltons arises effectively from an analyte present at a concentration of about fifty parts per billion.

The desorption profiles shown above were recorded using low-pressure and low-flow desorption conditions to enhance the concentration of the desorbed analyte in the carrier gas. These desorption profiles indicate that the concentration of $CCl_4$ in the desorption phase is about 550 times its concentration in the air sample.

Because the sampling times and the desorption times are nearly equal in this case (three and two seconds, respectively), the gain in concentration results almost entirely from the differences in pressures and flow rates during the sampling and desorption phases. The gain was measured by comparing the peak intensity of the desorption profile to the signal produced from direct introduction of the 3.4 ppm sample into the mass spectrometer. Each signal was corrected for background levels produced by a blank air sample, and the appropriate valves were adjusted so that the pressure in the mass spectrometer was $2 \times 10^{-5}$ Torr during both the desorption period and the direct sampling measurement. Because the total pressure in the mass spectrometer was the same in the two measurements, comparison of the background-corrected signals is a direct comparison of the relative concentrations.

The gain observed in this example is within a factor of two of the gain, G, calculated from comparison of the adsorption pressures, flows, and times, as set forth in Table III below:

TABLE III

|  | Sampling | Desorption |
|---|---|---|
| Average Pressure $<P>$ | 369 torr | 18.5 torr |
| Pressure Difference $\Delta P$ | 668 torr | 21 torr |
| Time | 3 sec | 2 sec (Full Width at Half Intensity) |
| Calculated Gain = 950 | | |

Figure 7:
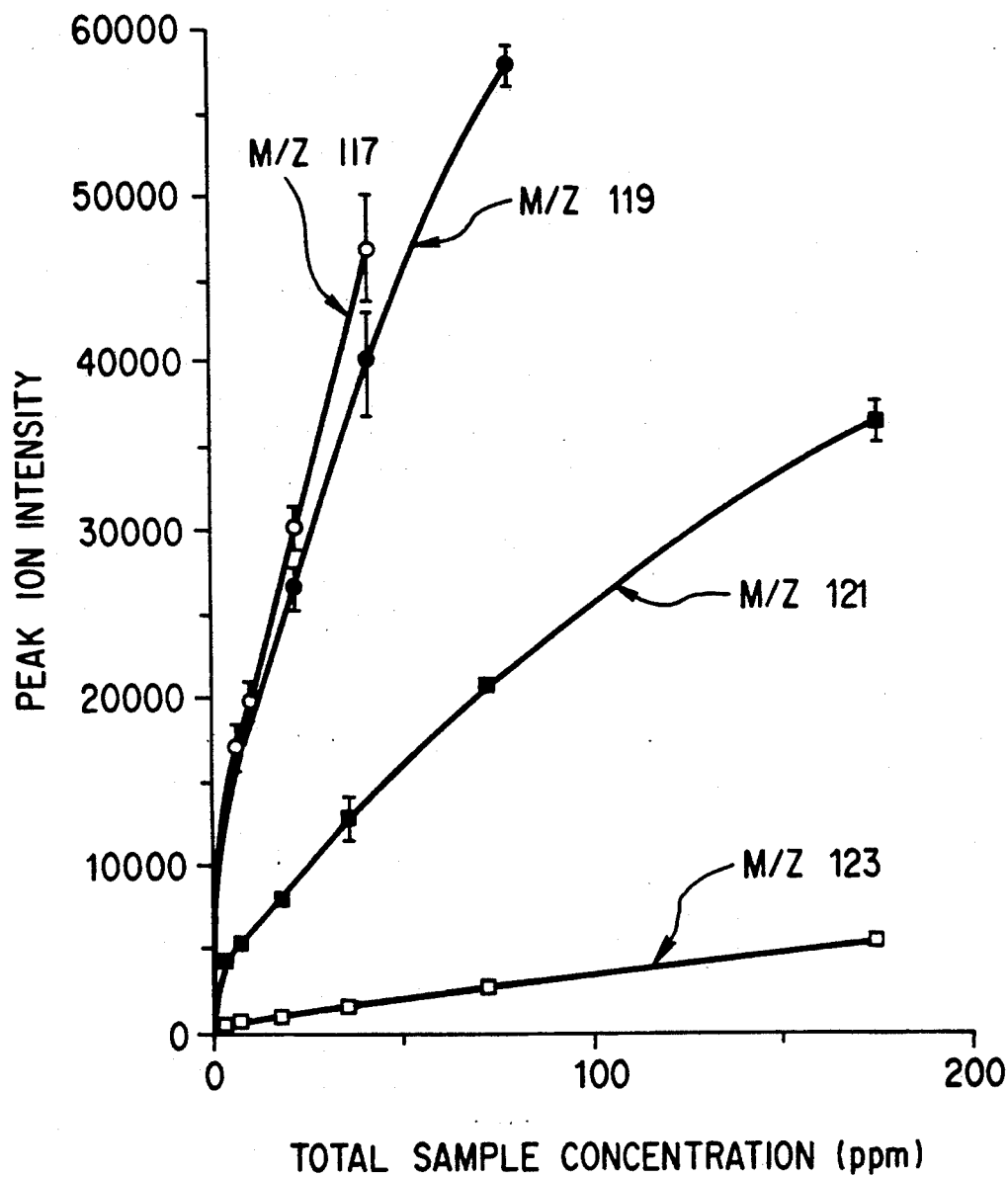
FIG. 7 shows the peak isotopic fragment ion signals during the desorption period as a function of the $CCl_4$ concentration in air.

The difference between the predicted and observed gains in this case results largely from saturation of the sorbent 10, as discussed above. FIG. 7, which shows the peak ion signals during the desorption period as a function of the $CCl_4$ concentrations for each monitored ion mass with plus/minus error bars, illustrates the effect of saturation. The desorbed signal for each $CCl_4$ isotopic fragmentation mass does not increase linearly with sample concentration.

Finally, equation (9) predicts that the gain G, and hence the ion intensity during the desorption phase, is inversely proportional to the average pressure in the sorbent tube during the desorption period.

Figure 8:
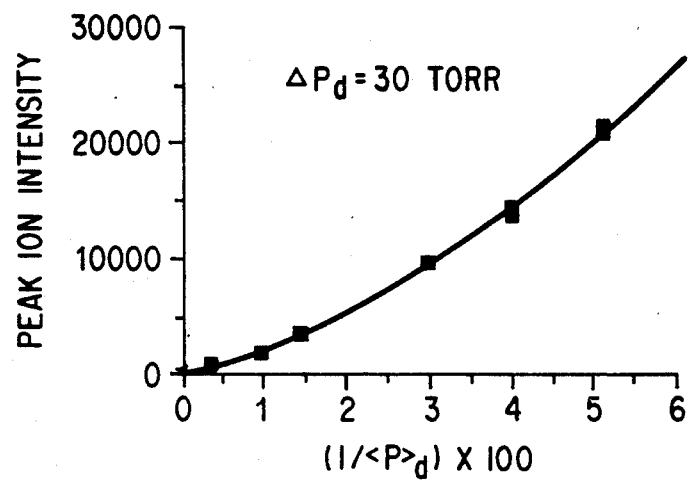
FIG. 8 shows the dependence of the peak intensity at mass 69 on desorption pressure for perfluorotributylamine sample in air.

In FIG. 8, the dependence of the peak intensity at mass 69 on the desorption pressure for a perfluorotributylamine sample in air is shown. The signal was measured as a function of the average pressure during the desorption period for constant sampling conditions (sample concentration, mass flow, and time) and a constant 30-torr pressure difference across the sorbent during the desorption period.

It is to be seen that the ion signal does increase with decreasing pressure (increasing $1/<P>_d$), as expected, but the signal does not increase linearly with $1/<P>_d$. This discrepancy results, at least in part, from the fact that the observed temporal profile of the desorption peak depends on the pressure. The observed peak width increased with increasing pressure, presumably because of slower heating at higher pressures and flow rates contributed to the non-linear response of the signal to $1/<P>_d$.

Although we have described the preferred embodiments of our invention, it is to be understood that it is capable of other adaptations and modifications within the scope of the appended claims.

Having disclosed our invention, what we claim as new and to be secured by Letters Patent of the United States is:

1. A method of preconcentrating trace constituents in a gas for subsequent analysis which comprises the steps of:
   A adsorbing at least one of the trace constituents onto a confined sorbent material for a predetermined period of time from a sample gas moving at a predetermined gaseous mass flow rate;
   B confining said sorbent material in a sealed space which includes an inlet of a detector means for receiving said one trace constituent; and
   C desorbing said one trace element from said sorbent material for a predetermined period of time into a carrier gas moving at a predetermined gaseous mass flow rate which is substantially less than the gaseous mass flow rate of said sample gas whereby the desorbed amount of said one trace constituent relative to said carrier gas that contains said desorbed trace constituent is substantially greater than the same amount of said one trace constituent relative to the portion of said sample gas that contained said trace constituent.

2. A method in accordance with claim 1, wherein said carrier gas containing said one trace constituent is introduced into said detector means through said inlet.

3. A method in accordance with claim 2, wherein said detector means comprises a mass spectrometer.

4. A method in accordance with claim 1, wherein the pressure of said carrier gas is substantially less than the pressure of said sample gas.

5. A method in accordance with claim 4, wherein said sample gas is substantially at or near ambient atmospheric pressure.

6. A method in accordance with claim 1, wherein said sample gas is air.

7. A method in accordance with claim 1, wherein said sorbent material is composed of particles of a solid material which are confined within a glass tube.

8. A method in accordance with claim 1, wherein said one trace constituent is caused to desorb from said sorbent material by heating said sorbent material.

9. A method in accordance with claim 8, wherein said carrier gas is preheated to assist in the desorption of said one trace constituent from said sorbent material.

10. A method in accordance with claim 1, wherein said carrier gas is air.

11. A method in accordance with claim 1, wherein said carrier gas does not chemically react with said one trace constituent.

12. A method in accordance with claim 1, wherein said carrier gas chemically reacts with said one trace constituent to produce a derivative of said one trace constituent that facilitates its detection by said detector means.

13. A method in accordance with claim 1, wherein a plurality of confined sorbent materials are provided in parallel with sealing means for each whereby one or more of said plurality of adsorbent materials may be used selectively to receive said sample gas and to desorb said carrier gas for analysis by said detector means.

14. A method in accordance with claim 3, wherein said mass spectrometer includes an electron-impact ionization ion source operatively connected to said inlet.

15. A method in accordance with claim 3, wherein said mass spectrometer includes a chemical ionization ion source operatively connected to said inlet.

16. A method in accordance with claim 15, wherein said carrier gas is a reagent gas for chemical ionization.

17. A method in accordance with claim 3, wherein said mass spectrometer includes a gas discharge ion source operatively connected to said inlet to operate at a pressure less than atmospheric pressure.

18. A method in accordance with claim 17, wherein a portion of said carrier gas entering said gas discharge ion source is removed therefrom by a vacuum pump and the remainder of said carrier gas is drawn through an aperture into the high vacuum of said mass spectrometer.

19. An apparatus for preconcentrating trace constituents in a gas to facilitate their analysis which comprises:
a sorbent material which is retained in a confined space and associated with means for selectively causing said sorbent material to adsorb or desorb said trace constituents;
a sample gas source and valve for introducing said sample gas onto said sorbent material and means for selectively opening and closing said valve;
a source of carrier gas connected to provide said carrier gas to said sorbent material;
pumping means for selectively lowering the pressure in said confined space containing said sorbent material;
a detector for detecting said trace constituents in said carrier gas;
a confined passageway from said carrier gas source to said detector through said sorbent material, whereby when said sorbent material desorbs said trace constituents received from said sample gas they can be carried by said carrier gas to said detector at a pressure substantially less than the pressure of said sample gas, whereby the ratio of the density of said trace constituents to mass of said carrier gas is substantially increased relative to the ratio of the density of said trace constituents for a comparable mass of said sample gas.

20. An apparatus in accordance with claim 19, wherein said detector comprises a mass spectrometer.

21. An apparatus in accordance with claim 20, wherein said mass spectrometer includes an electron-impact ionization ion source.

22. An apparatus in accordance with claim 20, wherein said mass spectrometer includes a chemical ionization ion source.

23. An apparatus in accordance with claim 22, wherein said carrier gas is a reagent gas to react with said trace constituents.

24. An apparatus in accordance with claim 20, wherein said mass spectrometer includes a gas discharge ion source that operates at a pressure less than atmospheric pressure.

25. An apparatus in accordance with claim 24, wherein a portion of said carrier gas entering said gas discharge ion source is removed therefrom by a vacuum pump and the remainder is removed through an aperture leading to a high vacuum in said mass spectrometer.

* * * * *